(12) United States Patent
Kanowitz (10) Patent No.: US 10,463,822 B2
(45) Date of Patent: *Nov. 5, 2019

(54) AIRWAY STABILIZATION SYSTEM (71) Applicant: Securisyn Medical, LLC, Highlands Ranch, CO (US)

(72) Inventor: Arthur Kanowitz, Littleton, CO (US)

(73) Assignee: Securisyn Medical, LLC, Highlands Ranch, CO (US)

(*) Notice: Subject to any disclaimer, the term of this patent is extended or adjusted under 35 U.S.C. 154(b) by 703 days.

This patent is subject to a terminal disclaimer.

(21) Appl. No.: 15/080,248

(22) Filed: Mar. 24, 2016

(65) Prior Publication Data

US 2016/0279367 A1 Sep. 29, 2016

Related U.S. Application Data

(60) Provisional application No. 62/137,518, filed on Mar. 24, 2015.

(51) Int. Cl.
*A61M 16/04* (2006.01)

(52) U.S. Cl.
CPC .................. *A61M 16/0497* (2013.01)

(58) Field of Classification Search
CPC .. A61M 16/0497; A61M 16/00; A61M 16/04; A61M 16/0488; A61M 16/049; A61M 16/0434; A61M 2205/6063; A61M 2205/583; A61M 39/00; A61M 39/1011; A61M 39/1016; A61M 39/12; A61M 2039/1061; A61M 2210/06; A61M 2202/0007; A61M 2202/0014; A61M 2202/02

USPC ...................................... 128/207.14, 207.15
See application file for complete search history.

(56) References Cited

U.S. PATENT DOCUMENTS

| | | | | |
|---|---|---|---|---|
| 4,527,559 A | * | 7/1985 | Roxburg | A61M 16/0488 128/207.17 |
| 4,690,138 A | * | 9/1987 | Heyden | A61M 16/04 116/324 |
| 5,259,371 A | * | 11/1993 | Tonrey | A61M 16/04 128/200.26 |
| 5,555,881 A | * | 9/1996 | Rogers | A61M 16/0488 128/207.14 |

(Continued)

*Primary Examiner* — Timothy A Stanis
*Assistant Examiner* — Matthew D Ziegler
(74) *Attorney, Agent, or Firm* — Glenn H. Lenzen; Dietze and Davis, PC (57) ABSTRACT

An airway device and a securing mechanism or faceplate each of which include active stabilizing components which prevent clinically significant movement of the airway device with respect to a patient's vocal cords in response to the application of significant forces in any direction to the airway device, be they longitudinal, torsional/rotational or bending. The improved airway device and faceplate each have interactive components that cooperate integrally with and engage one another to provide unparalleled strength and stability against movement. The securing mechanism includes a stabilizer adapted to releaseably engage or release a retention structure on the airway device to facilitate ease of application in all conditions. A mechanism attached to the airway device allows a secure connection of a 15 mm respiratory connector to the airway device while facilitating easy disconnection of the 15 mm connector from the airway device.

15 Claims, 10 Drawing Sheets

(56) References Cited

U.S. PATENT DOCUMENTS

| | | | | |
|---|---|---|---|---|
| 6,029,668 A * | 2/2000 | Freed | A61M 16/0488 128/200.26 |
| 9,023,059 B2 * | 5/2015 | Loushin | A61F 11/002 606/109 |
| 2002/0043597 A1 * | 4/2002 | Forsberg | A47B 9/04 248/188.8 |
| 2006/0174893 A1 * | 8/2006 | Kanowitz | A61F 5/055 128/207.14 |
| 2007/0066943 A1 * | 3/2007 | Prasad | A61M 1/3653 604/264 |
| 2009/0255538 A1 * | 10/2009 | Thomson | A61M 16/0488 128/207.17 |
| 2009/0308397 A1 * | 12/2009 | Neame | A61M 16/0488 128/207.17 |
| 2011/0240034 A1 * | 10/2011 | Ciccone | A61M 16/0493 128/207.17 |
| 2011/0284008 A1 * | 11/2011 | Kanowitz | A61M 16/0488 128/207.17 |
| 2012/0168571 A1 * | 7/2012 | Bond | A61M 16/0488 248/70 |
| 2012/0216803 A1 * | 8/2012 | Trodler | A61M 16/0497 128/200.26 |
| 2012/0227747 A1 * | 9/2012 | Levine | A61M 16/0497 128/207.14 |
| 2013/0276791 A1 * | 10/2013 | Kanowitz | A61M 16/0497 128/207.15 |
| 2014/0018732 A1 * | 1/2014 | Bagaoisan | A61M 25/0136 604/95.04 |
| 2014/0230823 A1 * | 8/2014 | Adams | A61M 16/0402 128/207.14 |

* cited by examiner

AIRWAY STABILIZATION SYSTEM

PRIORITY TO RELATED PATENT APPLICATIONS

This application is a U.S. Patent Application which claims the benefit of U.S. Provisional Patent Application Ser. No. 62/137,518 filed on Mar. 24, 2015, which is incorporated herein by reference.

FIELD OF THE INVENTION

The present invention relates generally to a new and improved airway stabilization system designed to maintain an airway in the trachea of a patient. Specifically, the present invention relates to a system for maintaining an airway device in a preselected position in a patient's trachea and for preventing clinically significant movement thereof and unintentional extubation of the patient in response to the application of significant multidirectional forces to the airway device. More specifically, the system of the present invention relates to two key elements of a safe and effective airway stabilization system: a new and improved airway device or endotracheal tube apparatus (ETT) and an improved securing device adapted to cooperatively interact with the improved airway device to facilitate rapid and simple application of the system, particularly in emergency situations, and to provide resistance against multidirectional forces of a significant magnitude that may be applied thereto.

BACKGROUND OF THE INVENTION

Endotracheal intubation is a medical procedure used to place an airway device (artificial airway) into a patient's trachea or airway. The use of an airway device is mandated in situations where an individual is unable to sustain the natural breathing function or maintain an open airway on his or her own due to unconsciousness, trauma, disease, drugs or anesthesia. Thus, life-saving mechanical ventilation is provided through the airway device which may be in the form of an endotracheal tube (ETT), or a supraglottic airway device such as a laryngeal mask airway (LMA), King Airway, or one of several other commercially available airway devices.

Endotracheal intubation is accomplished by inserting an airway device into the mouth, down through the throat and vocal cords or voice box, and into the trachea. This procedure creates an artificial passageway through which air can freely and continuously flow in and out of a patient's lungs and prevents the patient's airway from collapsing or occluding.

It is very important that the airway device be positioned correctly and maintained in the correct position in the trachea. If the device moves out of its proper position in the trachea and into either the right or left main stem bronchial tube, only one lung will be ventilated. Failure to ventilate the other lung can lead to a host of severe pulmonary complications. Moreover, if the airway device moves completely out of the trachea and into the pharynx, esophagus or completely outside the body, the patient will become hypoxic due to the lack of ventilation to the lungs, a condition which typically results in life-threatening brain injury within a matter of only a few minutes.

Even after an airway device has been positioned correctly, subsequent movement of the patient can lead to inadvertent movement of the device, as hereinabove described. An intubated patient may restlessly move about and may also attempt to forcibly remove an airway device, whether conscious or unconscious, particularly if the patient is uncomfortable or having difficulty breathing, which can lead to panic. Because medical emergencies may occur anywhere, emergency medical service personal (i.e., paramedics) may be called upon to insert airway devices in out-of-hospital emergency settings as well as in hospital settings by emergency department, operating room, and critical care clinicians. Therefore, such unintentional movement is not uncommon, particularly when the patient is moved from an out-of-hospital setting, such as an accident scene, to an emergency department of a hospital. Further, anytime an intubated patient may be moved, for example, not only from an ambulance to a trauma facility, but also from one hospital to another hospital, from one area of the hospital to another area in the same hospital (imaging, laboratory, operating theater), or from a hospital to an outpatient rehabilitation facility, unintentional movement of an airway device is a risk. Even repositioning an intubated patient in a hospital bed may cause unintentional movement of the endotracheal tube.

Inadvertent movement of an airway device may also occur as a result of moving external ventilation equipment, such as a conventional mechanical ventilator or bag valve mask. Typically, the external ventilation equipment is connected to the external end of the device by an air conduit to establish air flow to and from the lungs. Inadvertent pulling on, or other excessive movement of the air conduit, may transfer movement to the airway device, thereby shifting it from its proper position and causing unplanned extubation.

Unplanned extubation is a hazardous and costly problem which studies have demonstrated occurs at an unacceptably high rate. A study completed by Carson et al reports that approximately 950,000 patients are mechanically ventilated in the United States annually. Carson et al., *The Changing Epidemiology of Mechanical Ventilation: A Population-Based Study. Journal of Intensive Care Medicine.* 2006 February; 21(3): pp. 173-182. A review of the world-wide medical literature suggests that the world-wide rate of unplanned extubation averages approximately 7.31%. Lucas de Silva, *Unplanned Endotracheal Extubation in the Intensive Care Unit: Systematic Review, Critical Appraisal, and Evidence-Based Recommendations.* Anesth Analg 2012; 114:1003-14. Applying the world-wide average to the U.S. figure above, an estimated 68,000 patients in the United States alone experience an unplanned extubation each year. Such unplanned extubations are costly, not only for patients who experience increased rates of morbidity and mortality, but also for hospitals, physicians and insurance companies who incur the liability costs associated therewith. The annual intensive care unit (ICU) bed cost associated with unplanned extubations in the United States alone is estimated at $2.6 Billion, which includes imaging, pharmacy, and laboratory expenses. (Extrapolated using data from the Carson study referenced above and the cost of long-term care according to the U.S. Department of Health and Human Services National Clearinghouse for long-term care information. See also S. K. Epstein, M. L. Nevins & J. Chung, *Effect of Unplanned Extubation on Outcome of Mechanical Ventilation, Am. Journal of Respiratory and Critical Care Medicine,* 161: 1912-1916 (2000) which discusses the increased likelihood of long-term care outcome). Moreover, it is not unknown for jury damage awards in personal injury law suits arising from unplanned extubations to be in excess of $35 M. The high incidence of unplanned extubation and the associated increase in healthcare costs implies that an improved restraining system, which has the capacity to resist the application of greater forces which would otherwise result in movement of the airway device, is sorely needed.

Various prior art systems have attempted to address the problem of maintaining an airway device in the correct position and preventing unintentional extubation. The most common approach for securing an airway device (typically, an endotracheal tube) is with adhesive tape. Umbilical tape may be used as an alternative. Both present the same challenges. The tape is tied around the patient's neck and then wrapped and tied around the smooth outside surface of the endotracheal tube itself. Arranged in this fashion, the tape is intended to anchor the endotracheal tube to the corner of the patient's mouth and prevent its unintentional movement. While the use of tape in this manner provides some benefit, the restraint available from the tape usually diminishes because the tape becomes covered and/or saturated with blood, saliva, or other bodily fluids. Consequently, the endotracheal tube may be readily moved from its preferred position in the patient's trachea, and this form of securing an airway device provides inadequate protection against movement resulting from the application of multidirectional forces such as bending, torsional/rotational or substantial lateral forces to the device. Such forces may exceed fifty (50) pounds in magnitude, and, as shown in the results of two studies of the restraint capabilities of current devices and methods set forth in Tables 1 and 2 below, such devices and methods do not provide sufficient resistance to prevent unplanned extubation. Clinically significant movement is defined as longitudinal movement of the airway device in a direction towards or away from the patient's mouth to a point where the tip of the airway device has moved beyond the vocal cords. Typically, such movement is in the range of five (5) to seven (7) centimeters.

Restraint Capabilities of Current Devices and Methods

TABLE 1

|  | Median | Min | Max |
| --- | --- | --- | --- |
| Thomas Tube Holder | 12.98 | 2.64 | 22.44 |
| Adhesive Tape | 19.58 | 3.96 | 39.6 |
| Non Adhesive Tape | 7.48 | 2.42 | 27.72 |

Force to Extubate (7 cm movement) in Lbs
Owens, et al. Resuscitation (2009)

TABLE 2

|  | Median | Min | Max |
| --- | --- | --- | --- |
| Adhesive Tape (Lillehei) | 19.5 | 15 | 25 |
| Tube Tamer | 12.9 | 10 | 15 |
| Precision Medical | 8.6 | 7 | 10 |
| Biomedix Endogrip | 10.7 | 6 | 12 |
| Thomas Tube Holder | 37 | 28 | 43 |

Force to Extubate (2 cm movement) in Lbs
Carlson, et al. Annals of Emergency Medicine 2007

U.S. Pat. No. 5,353,787 issued Oct. 11, 1994, to Price discloses an apparatus having an oral airway for providing fluid communication for the passage of gas from a patient's mouth through his or her throat and into the trachea, the oral airway being releaseably attached to an endotracheal tube for use in combination therewith. While Price's apparatus eliminates the smooth surface of the tube and resists longitudinal movement in relation to the oral airway, the system disclosed by Price does not address the above-identified problem of resisting multidirectional forces. Moreover, Price's device cannot prevent clinically significant movement of an airway device in relation to the vocal cords and an unplanned extubation resulting therefrom.

Other attempts to solve the aforementioned problems have employed auxiliary mechanical securing devices to maintain the position of an endotracheal tube in a patient. Many of these auxiliary mechanical devices include some type of faceplate which is attached to the patient's face, usually with one or more straps that extend around the back of the patient's head or neck. The faceplate includes some type of mechanical contact device that grips the smooth surface of the endotracheal tube. Typical mechanical contact devices include thumb screws, clamps, adhesives, locking teeth, and straps. By way of example, U.S. Pat. No. 4,832,019 issued to Weinstein et al. on May 23, 1989, discloses an endotracheal tube holder which includes a hexagonally-shaped gripping jaw that clamps around the tube after it has been inserted into a patient's mouth and a ratchet-type locking arrangement designed to retain the gripping jaw in position around the tube. Weinstein's patent disclosure states specifically that the tube will not be deformed. However, the fundamental mechanics of a hexagonal receptacle applied around a cylindrical tube to stabilize it reveal that the hexagonal structure will not impart force to the tube of sufficient magnitude to prevent longitudinal movement. However, it has been found that if sufficient pressure is applied directly to the tube by the gripping jaw, the tube will deform or even crush, thereby decreasing ventilatory efficiency to the point that airflow to the patient's lungs will be restricted or even cut off, an extremely serious problem.

U.S. Pat. No. 7,568,484 issued on Aug. 4, 2009, and U.S. Pat. No. 7,628,154 issued on Dec. 8, 2009, both to Bierman et al., disclose endotracheal tube securement systems which include straps extending from the corners of a patient's mouth above and below the patient's ears on each side of the patient's head. However, the devices disclosed in the '484 and the '154 patents merely retain the position of the tube in the patient's mouth and cannot prevent movement thereof in various directions, either longitudinally, rotationally or laterally, as hereinabove described.

Specifically, to maintain an effective restraint, attending medical personnel increase the amount of clamping force applied on an airway device. Increasing the amount of clamping force to an effective level may pinch the device to the point where a portion of the inner tube diameter (and hence air passageway) is significantly restricted. Restricting the cross-sectional size of the air passageway decreases the ventilatory efficiency of the tube, thereby decreasing the respiratory airflow. The restriction of the cross-sectional size of the air passageway creates resistance to both inspiratory airflow and expiratory airflow. Insufficient airflow during inspiration can lead to hypoxemia, which is problematic, but can be overcome by increasing the positive pressure of the ventilation source. However, during expiration, any increased pressure due to constriction or decreased tube diameter, increases the amount of work a patient must perform to simply exhale. Increased pressure can also lead to barotrauma in the lungs and resistance to expiratory airflow can lead to multiple other adverse effects within the lungs. Impairing a patient's ventilations may result in serious medical effects, particularly with patients whose functions are already compromised. Therefore, the ability for clinicians to adequately stabilize an airway device for prevention of unplanned extubation without constriction of the air passageway is crucial for patient safety.

Endotracheal tubes have a standard respiratory connector that serves as a conduit between the endotracheal tube and artificial ventilator for the purpose of maintaining a continuous flow of air from the ventilation source to the patient's lungs. Standard connectors must be tightly seated into the endotracheal tube to avoid unintentional disconnection of the ventilation source from the endotracheal tube during mechanical breathing. When tightly seated, the connector is often difficult for the clinician to remove from the endotracheal tube, when necessary. Therefore, an airway device with a connector that prevents unintentional disconnection, yet allows for quick and easy intentional connection and disconnection is needed.

More recently, U.S. Pat. No. 8,001,969 issued on Aug. 23, 2011, and U.S. Pat. No. 8,739,795 issued on Jun. 3, 2014, both to Arthur Kanowitz, the inventor of the present invention, disclose airway stabilization systems which address many of the problems set forth above. On-going clinical trials of these devices and continuing research into ways of providing even more advanced and rapidly deployable airway stabilization systems have resulted in yet further improvements to the overall design of the system components.

In view of the above, it will be apparent to those skilled in the art from this disclosure that a need exists for an improved airway stabilization system which not only protects an airway device from occlusion and crushing, but also is easier to apply to a patient while at the same time maintains the device in its preferred position in a patient's trachea and prevents clinically significant movement thereof with respect to the vocal cords as a result of the application of multidirectional forces of significant magnitude thereto. The present invention addresses these needs in the art as well as other needs, all of which will become apparent to those skilled in the art from the accompanying disclosure.

SUMMARY OF THE INVENTION

In order to address the aforementioned needs in the art, a complete airway stabilization system is provided which may be fitted to any airway device to maintain an airway in a patient's trachea and which prevents clinically significant movement of the airway device with respect to a patient's vocal cords in response to the application of forces in any direction to the device, be they longitudinal, torsional/rotational or bending.

Unlike conventional prior art devices which employ an airway device that is passive in the stabilization process, for example, an endotracheal tube and an active stabilizer, the system disclosed herein comprises an improved airway device that is active in the stabilization process and an improved securing apparatus or stabilizer, also active in the stabilization process. Thus both devices have active stabilization components that cooperate integrally with and engage one another to provide unparalleled strength and stability against movement, even when the endotracheal tube becomes slippery from fluids and/or secretions. Moreover, the system of the instant invention provides the above-referenced strength and stability without applying any constricting pressure whatsoever to the airway device itself. The airway device has a continuous sidewall extending between a proximal and a distal end portion thereof which defines a hollow conduit through which the airway is established. A retention collar on the airway device, also referred to as the KAD-collar, positioned on the airway device on the exterior of the sidewall between the end portions thereof. The KAD-collar may also be formed integrally with the airway device. The KAD-collar extends along a predetermined length of the sidewall at a predetermined fixed position relative to the distal end of the airway device (and outside of a patient's oral cavity so as to minimize risk of oral and/or dental injury to the patient) to locate the MD-collar within the confines of a stabilizer and to cooperate therewith to maintain the distal end of the airway device at the correct position in the trachea relative to the carina to establish the airway. The KAD-collar includes a plurality of restraints or ribs extending circumferentially about the collar. The ribs provide an active surface area forming a tight interlocking fit with cooperating interlocking portions or channels of a the stabilizer secured to a patient, thereby establishing a complete barrier against movement which would otherwise result from forces applied to the device as hereinabove described.

A securing apparatus or stabilizer includes a faceplate which is secured to the patient and a restraining tower which is configured to cooperate with the interacting endotracheal tube restraining device or KAD-collar to prevent clinically significant movement of the distal end of the airway device with respect to the vocal cords of the patient in response to various multidirectional loads or forces of a significant magnitude which may be applied to the airway device during movement of the patient or by the patient himself. Unlike prior art devices, the faceplate is formed of a single member to allow greater ease of application, the member being structured and arranged to be secured over the face of a patient and being operatively connected to the restraining tower while, at the same time, providing ease of access to the patient's oral cavity for administration of medications and oral hygiene.

The restraining tower is secured to the faceplate and extends outwardly therefrom in a direction away from a patient's face. The restraining tower is adapted to retain the airway device via releasable engagement with the KAD-collar secured thereto in an internal cavity which is also structured and arranged to contain any potential points of kinking or failure in the tubular body of the airway device outside the patient's oral cavity, thereby minimizing the possibility of oral or dental injury.

In an embodiment, a securing apparatus is provided which may be installed and/or removed from an airway device positioned previously in a patient's airway without interrupting ventilation of the patient.

In an embodiment, an endotracheal tube assembly is provided that further includes a locking mechanism that is adapted to quickly and releaseably secure a respiratory or 15 mm connector to the endotracheal tube assembly via a simple twisting motion These and other features, aspects and advantages of the present invention will become apparent to those skilled in the art from the following detailed description of preferred embodiments taken in connection with the accompanying drawings, which are briefly summarized below, and by reference to the appended claims.

BRIEF DESCRIPTION OF THE DRAWINGS

Referring now to the attached drawings which form a part of this original disclosure:

FIG. 6.A. is a side elevation view of the retention structure or KAD-collar of the present invention affixed to a 6.0 mm airway device in accordance with an embodiment;

FIG. 6.B. is a side elevation view of the retention structure or KAD-collar of the present invention affixed to a 6.5 mm airway device in accordance with an embodiment;

FIG. 6.C. is a side elevation view of the retention structure or KAD-collar of the present invention affixed to a 7.0 mm airway device in accordance with an embodiment;

FIG. 6.D. is a side elevation view of the retention structure or KAD-collar of the present invention affixed to a 7.5 mm airway device in accordance with an embodiment;

FIG. 6.E. is a side elevation view of the retention structure or KAD-collar of the present invention affixed to an 8.0 mm airway device in accordance with an embodiment;

FIG. 7.A. is a side elevation view of the positioning of a 7.5 mm endotracheal tube within the securing tower of the airway stabilization system of the present invention in a patient having an airway of approximately 20 cm in length;

FIG. 7.B. is a side elevation view of the positioning of a 7.5 mm endotracheal tube within the securing tower of the airway stabilization system of the present invention in a patient having an airway of approximately 22 cm in length;

FIG. 7.C. is a side elevation view of the positioning of a 7.5 mm endotracheal tube within the securing tower of the airway stabilization system of the present invention in a patient having an airway of approximately 24 cm in length;

FIG. 7.D. is a side elevation view of the positioning of a 7.5 mm endotracheal tube within the securing tower of the airway stabilization systems of the present invention in a patient having an airway of approximately 26 cm in length;

FIG. 8.A. is a side elevation view of a locking mechanism for releaseably securing a 15 mm respiratory connector to an airway device of an airway stabilization system in accordance with an embodiment;

FIG. 8.B. is a side elevation view of the locking mechanism of FIG. 8.A. showing a 15 mm respiratory connector secured to an airway device of an airway stabilization system in accordance with an embodiment;

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
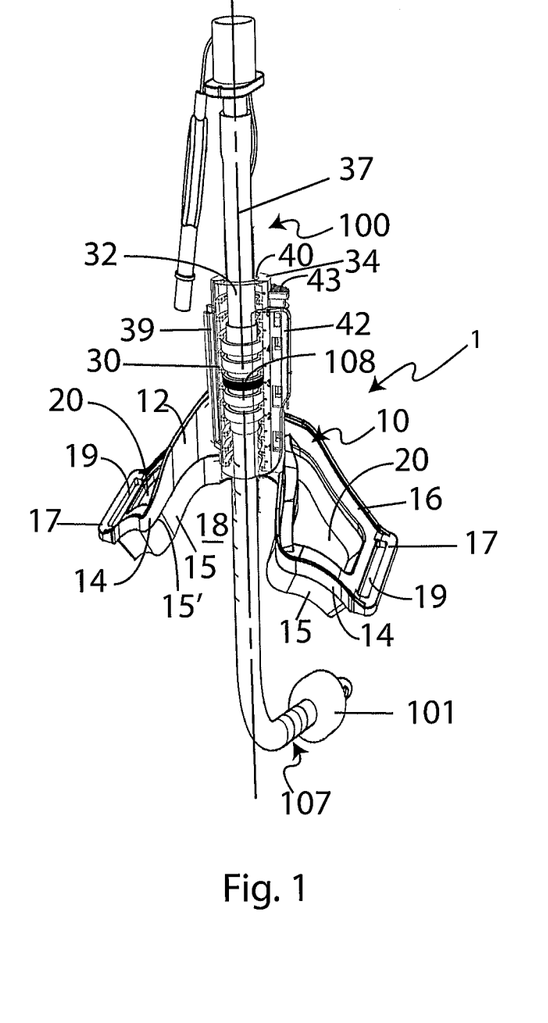
FIG. 1 is a side perspective view of an airway stabilization system according to an embodiment of the present invention.
Figure 2:
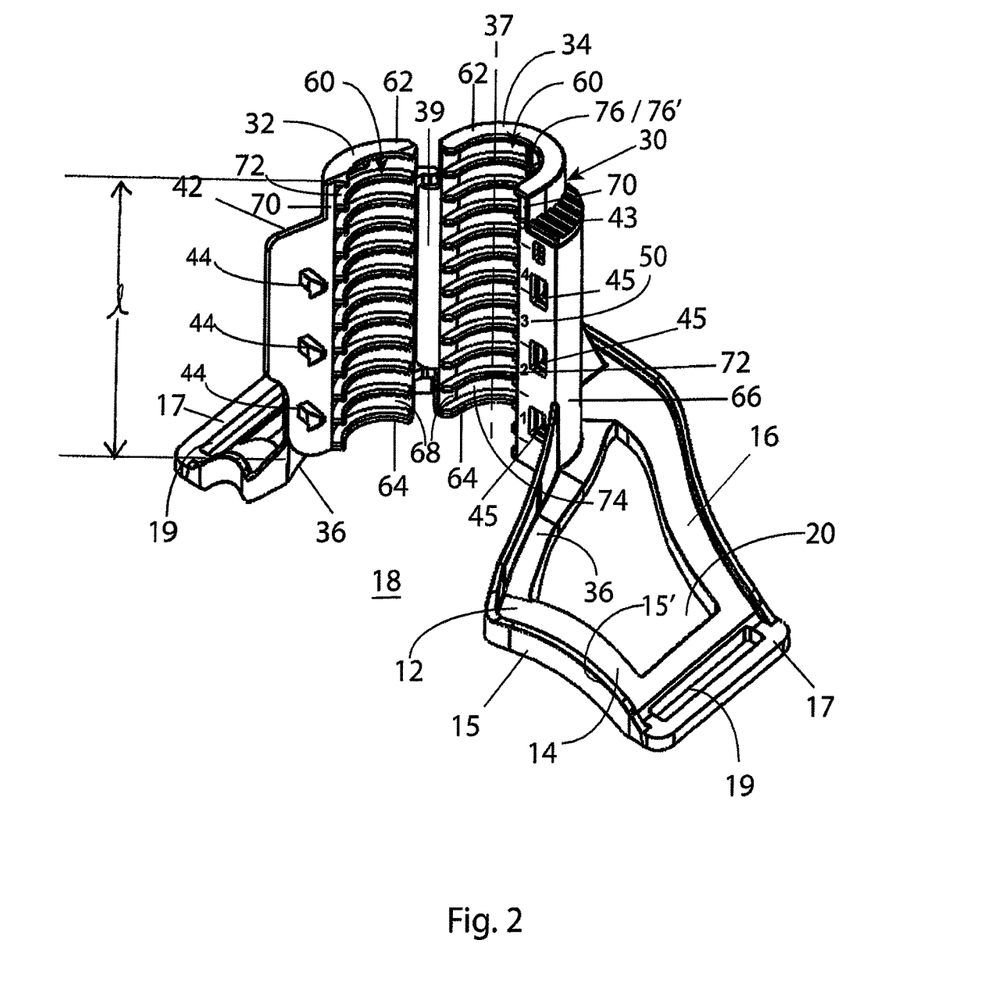
FIG. 2 is a side perspective view of a securing apparatus or stabilizer of an airway stabilization system of the embodiment of FIG. 1 shown in an open position to more clearly illustrate the elements thereof.

Referring initially to FIGS. 1 and 2, an airway stabilization system shown generally at numeral 1 is illustrated in accordance with an embodiment of the present invention. The airway stabilization system is used to maintain an airway in a patient under conditions where natural respiration is impossible or severely compromised. The airway stabilization system includes a stabilizer 10 and an airway device depicted generally at 100, the stabilizer and airway device cooperating to maintain an air passageway to a patient's lungs via the patient's mouth, oral cavity, throat, past a patient's vocal cords into a patient's trachea and bronchial tubes connected thereto for respiration of the patient. By way of example and not of limitation, the airway device may be in the form of an endotracheal tube (ETT) as shown in the accompanying figures or an adaptation of one of several commercially available endotracheal tubes or an adaptation of one of several commercially available supraglottic airway devices such as a King LT™ airway device manufactured by King Systems, Noblesville, Ind. or a laryngeal mask airway (LMA) such as a LMA Classic™ manufactured by LMA North America, San Diego, Calif. The adaptation requires incorporation of a series of alternating ribs and recesses into the device to interact with a cooperating ribbed and recessed restraining tower 30 of the stabilizer, as will be described in greater detail below.

As illustrated and discussed with respect to FIGS. 9 and 10 below, the airway stabilization system, which includes the stabilizer 10, fits over a patient's face 31 and mouth 33 below a patient's nose 35, and the airway device, whatever its form, is placed through the patient's mouth into his or her trachea, the components thereof cooperating with one another to maintain an airway to the patient's trachea and lungs for critical ventilation of the patient. The stabilizer 10 of the airway stabilization system includes a faceplate 12 which may be secured to the patient's face by suitable attachment means or apparatus, by way of example and not of limitation, non-stretchable straps 13 (FIGS. 9 and 10) extending around the patient's head and securable by buckles, hook and loop fasteners known commonly as Velcro® or other suitable attachments, as is known in the art.

Referring again to FIGS. 1 and 2, the faceplate is preferably of unitary construction and in a generally symmetrical mask-like configuration contoured to permit it to conform to a patient's face when it is secured in position. It may be formed of plastic, rubber, metal, composite material or other suitable materials having the desired physical properties for the application. The faceplate 12 includes an upper (maxillary) portion 14, an oppositely disposed lower (mandibular) portion 16, the upper and lower portions being interconnected by a pair of oppositely disposed, spaced apart end portions 17, each end portion having an aperture or slot 19 formed therein and adapted to receive securing apparatus 13. The upper, lower and end portions define a plane 18 and apertures 20 adapted to be positioned over a patient's respective cheek areas 21, thus allowing the device to fit over a patient's face like a mask as described above while yet permitting access to the patient's face, mouth and oral cavity for administering medications and performing oral hygiene. The faceplate is generally symmetric about a patient's oral cavity and nose, thereby facilitating ease of positioning thereof on a patient's face.

A ribbed restraining device or tower 30 includes a pair of oppositely disposed c-shaped collars 32 and 34 respectively extending generally symmetrically about and along axis 37 in a direction substantially perpendicular to the plane 18 of the faceplate 12 and away from the patient's face. Collar 34 includes a pair of oppositely disposed members or legs 36, the legs extending radially outwardly therefrom in opposite directions and generally parallel to the plane 18 of the stabilizer and operatively connected to the upper and lower sections 14 and 16 thereof. In an embodiment, the faceplate may include a cushioning layer 15 formed of rubber, foam or other suitable material affixed to a bottom side 15' of each of the upper and lower portions 14, 16 of the faceplate and legs 36 and adapted to be positioned intermediate the faceplate and a patient's face. In operation. the collars 32 and 34 are pivotally interconnected, for example, by hinge member 39 and are moveable into mating contact with one another, thereby forming a cavity 40 adapted to releaseably engage a retention structure or collar secured to the airway device, as will be described in greater detail below. Each of the collars includes a snap, clip, latch, camming operating apparatus or other suitable interlocking feature 42 having one or more locking members 44 adapted to releasably engage corresponding mating locking members 45 formed in or secured to the other juxtaposed collar to releaseably clamp them together circumferentially around the airway device in stabilizing and supporting engagement therewith. A release mechanism, for example, a quick-release actuator or button 43, allows the c-collars to be easily and rapidly released from locking engagement with one another to facilitate positioning and adjustment of the stabilizer with respect to the restraining device. Once the airway device is positioned at the desired depth in a patient's trachea, the stabilizer is secured around the patient's head. A plurality of spaced apart reference markings or depth guides 50 are formed on c-collar 34 which are structured and arranged to cooperate with other features of the system for ease of monitoring the relative position of the airway device with respect to the restraining tower, as defined more specifically below.

The elements of the c-shaped collars 32 and 34 are shown in greater detail in FIG. 2; although for ease of illustration, the details of only one collar, collar 34, will be described. It is to be understood that collar 32 is of substantially identical mirror image construction thereto. Collar 34 defines a semi-cylindrically shaped cavity 60 about the longitudinal axis 37, each cavity having first and second end portions 62 and 64, an outer surface 66, an inner surface 68 and a pair of generally parallel extending edge surfaces 70. Each of the collars 32, 34 includes a plurality of spaced-apart annular flanges 72 extending substantially radially inwardly from the inner surface 68 thereof, each annular flange cooperating with an adjacent annular flange to define a structural recess 74 therebetween. As discussed below in greater detail, the inwardly extending annular flanges and structural recesses are structured and arranged to releaseably engage corresponding mating structural recesses 124 and outwardly extending annular flanges or ribs 122 of the airway device retention collar, also referred to as a KAD-collar (shown as element 120 in FIGS. 3-5, 6.A.-6.E., 7.A.-7.D, 8.A. and 8.B.), thereby creating multiple points of contact and interaction between the stabilizer and the airway device and thus preventing clinically significant movement of the airway device in response to substantial forces which may be applied thereto in any direction. The retention structure and securing apparatus cooperate to completely encapsulate the airway device whereby the airway device is isolated totally from any constricting, pinching, or crushing forces that would constrict an inner diameter thereof, thereby also restricting ventilation of a patient. The multiple points of contact and interaction between the stabilizer and the retention structure are created by at least one of the pivotally interconnected c-collars, for example c-collar 32 into locking engagement with the other of the pivotally interconnected c-collars 34. Advantageously, in accordance with an embodiment of the instant invention, unlike prior art securing devices, the system herein disclosed may be secured laterally from a side of an airway device without being placed over the end of the device and, therefore, without disconnecting a ventilation source or interrupting ventilation of a patient.

In the embodiment of the airway stabilization system shown in FIGS. 1 and 2, the system further includes structural members which prevent the rotation of an airway device after it has been inserted in a patient's airway. In this embodiment, the rotation prevention members include a vertical bar 76 formed in the inner surface 68 of c-shaped collar 32 and extending intermediate the first and second end portions 62 and 64. The bar is adapted to receive a vertically extending channel 123 formed on the KAD-collar 120 operatively connected to an airway device 100, all of which is shown in greater detail in FIG. 4. Although not visible in the drawings, optionally, a second channel substantially identical in size and configuration to channel 123 may be formed on the opposite site of the KAD-collar there from. When the c-collars 32, 34 are secured together in clamping engagement with the KAD collar secured to an airway device such as the airway device 100 of FIG. 3, the vertical rib 76 is positioned within the corresponding vertical channel 123, the rib and channel cooperating with one another to lock the airway device in place to prevent rotation thereof in the patient's throat and airway without constricting the airway device to accomplish the anti-rotation.

Figure 3:
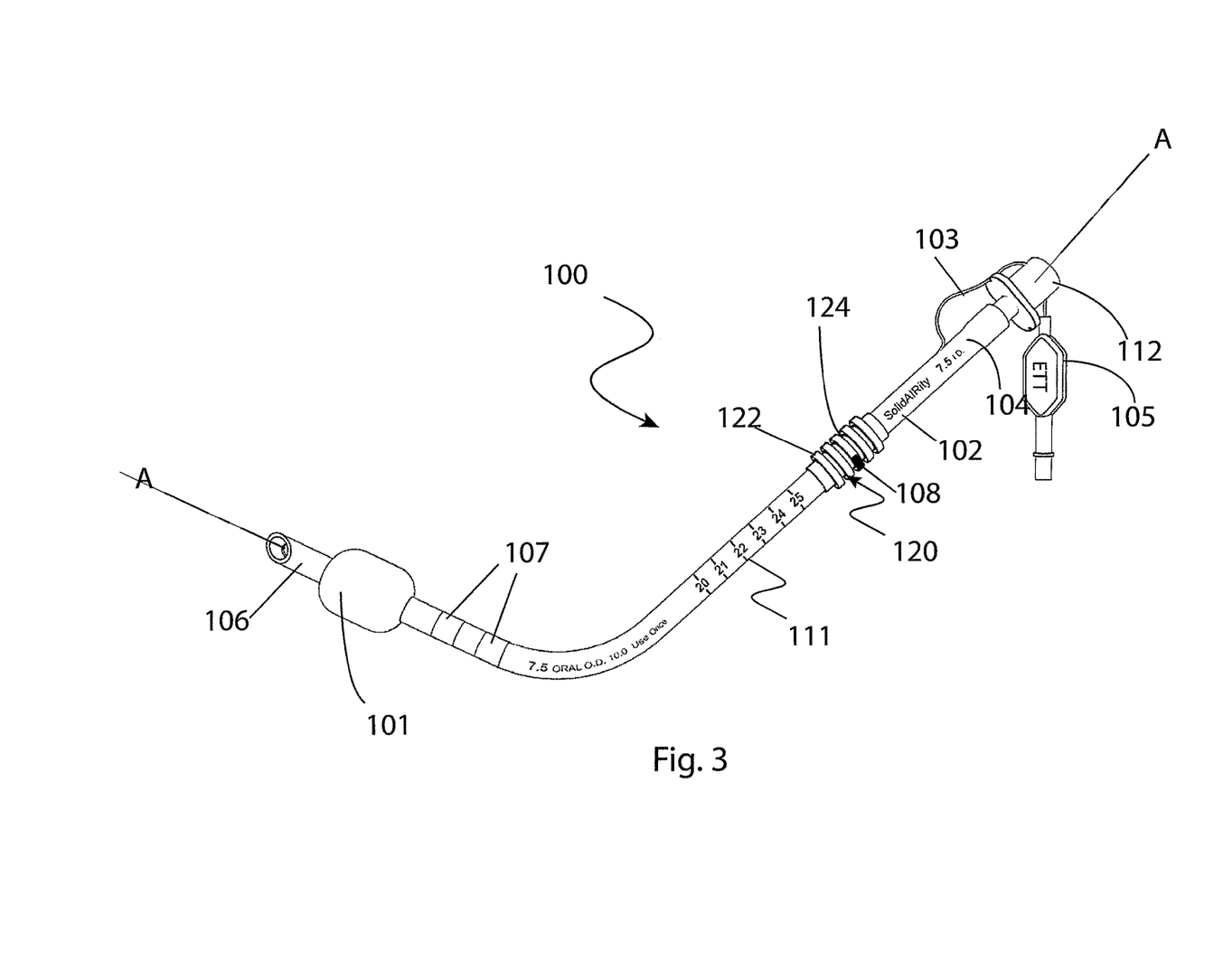
FIG. 3 is a side elevation view of an airway device portion of the airway stabilization system of the present invention in accordance with an embodiment.
Figure 4:
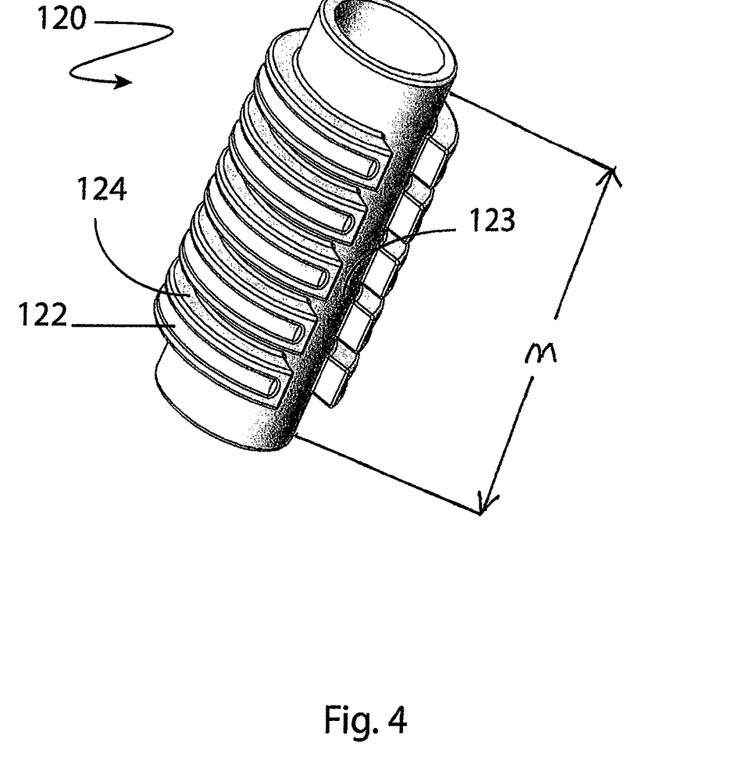
FIG. 4 is a side perspective view of a retention structure or KAD-collar of the present invention in accordance with an embodiment.
Figure 5:
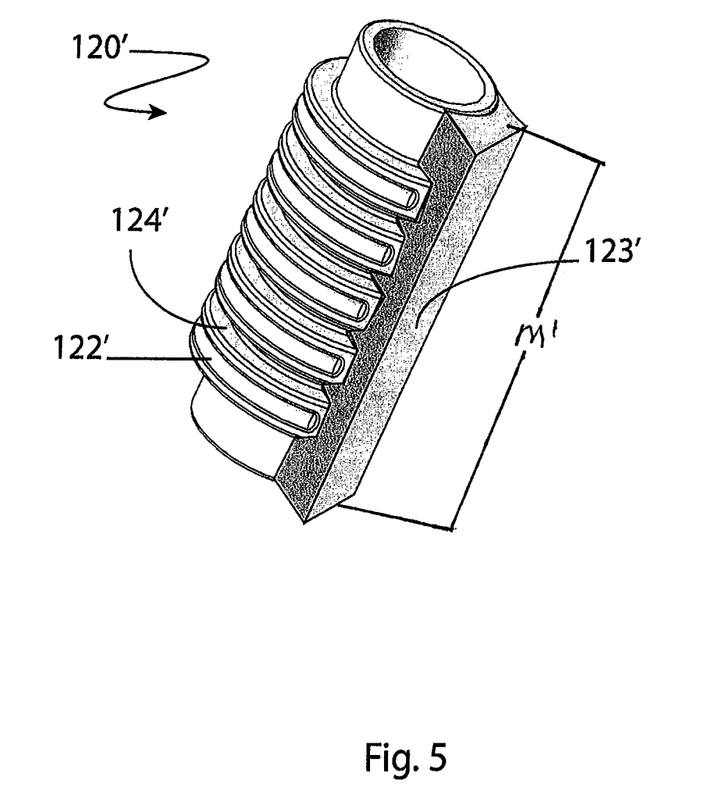
FIG. 5 is a side perspective view of a retention structure or KAD-collar of the present invention in accordance with another embodiment.

Referring now to FIG. 5, in another embodiment of the present invention, a retention or KAD-collar 120' is shown in which the vertically extending channel 123 of the embodiment of FIG. 4 is replaced by a vertically extending rib 123'. In this embodiment, vertically extending rib 76 formed in the inner surface 68 of c-shaped collar 34 in the embodiment of FIG. 4 would be replaced by a vertically extending channel 76'. Channel 76' is structured and arranged to receive the vertically extending rib 123'. When the c-collars 32, 34 are secured together in clamping engagement with the KAD collar secured to an airway device such as the airway device 100 of FIG. 3, the rib 123' is positioned within the corresponding vertical channel 76', the rib and channel cooperating with one another to lock the airway device in place to prevent rotation thereof in the patient's throat and airway without constricting the airway device to accomplish the anti-rotation.

Turning now to FIGS. 3-5, 6.A.-6.E., 7.A.-7.D, 8.A. and 8.B., the details of embodiments of an airway device 100 of the present invention are shown in greater detail. By way of example and not of limitation, the airway device is shown in the form of endotracheal tubes of various sizes as defined by their internal diameters in millimeters, as is known in the art and discussed in greater detail in applicant's published patent application, U.S. Patent Application Pub. No. US 2013/0276791, published Oct. 24, 2013. As best shown in FIG. 3, the airway device 100 includes a flexible member or body portion 102 having a tubular shape of a preselected length and preselected internal and external diameters extending along an axis A. The body 102 extends intermediate and is operatively connected to a proximal end portion 104, which refers to the end of the airway device that is connected to an oxygen supply and is also referred to in the art as the machine end, and a distal end portion 106 at the patient end of the airway device. The proximal end portion 104 is sized and configured to mate with a distal end portion 110 of a respiratory connector 112, also referred to as a 15 mm connector, as shown in FIGS. 8A. and 8.B. The end portion 110 of the 15 mm connector includes a circumferentially extending retention flange 114 secured thereto for retaining a freely-rotating internally threaded cap 113 on the end 110. The airway device includes a flange or wing member 116 extending circumferentially around the proximal end 104 thereof which interacts and cooperates by threadably engaging with threads 113' in the threaded cap in securing the 15 mm connector to the airway device after the distal end 110 of the connector is inserted into the proximal end 104 of the body portion 102. The flange 116 may be formed integrally with the body of the airway device or may be secured thereto by chemical bonding or other suitable means. By twisting the cap in a clockwise direction, the 15 mm connector may be locked onto the airway device as illustrated in FIG. 8.B. To unlock the connector, the cap is simply twisted in a counterclockwise direction.

Referring back to FIG. 3, the airway device 100 includes a balloon 101, a balloon inflation tube 103, a balloon inflation pilot (which indirectly indicates the pressure in the balloon 101) and one-way valve 105, a plurality of insertion depth reference markers 111 affixed to the mid-body, a series of insertion depth mark indicators or bands 107 affixed to a distal end portion thereof, and a retention member or KAD-collar 120 extending circumferentially about the body portion 102 coaxially therewith and disposed at a preselected position thereon. A significant improvement over the prior art, the depth mark indicators 107 of the present invention are luminescent in color, for example, a bright yellow, instead of the conventional light-absorbing black. The bright luminescent color readily reflects the light of a light source such as a laryngoscope, thereby making the bands highly visible in a patent's airway and facilitating accurate positioning of the airway device.

Figure 6:
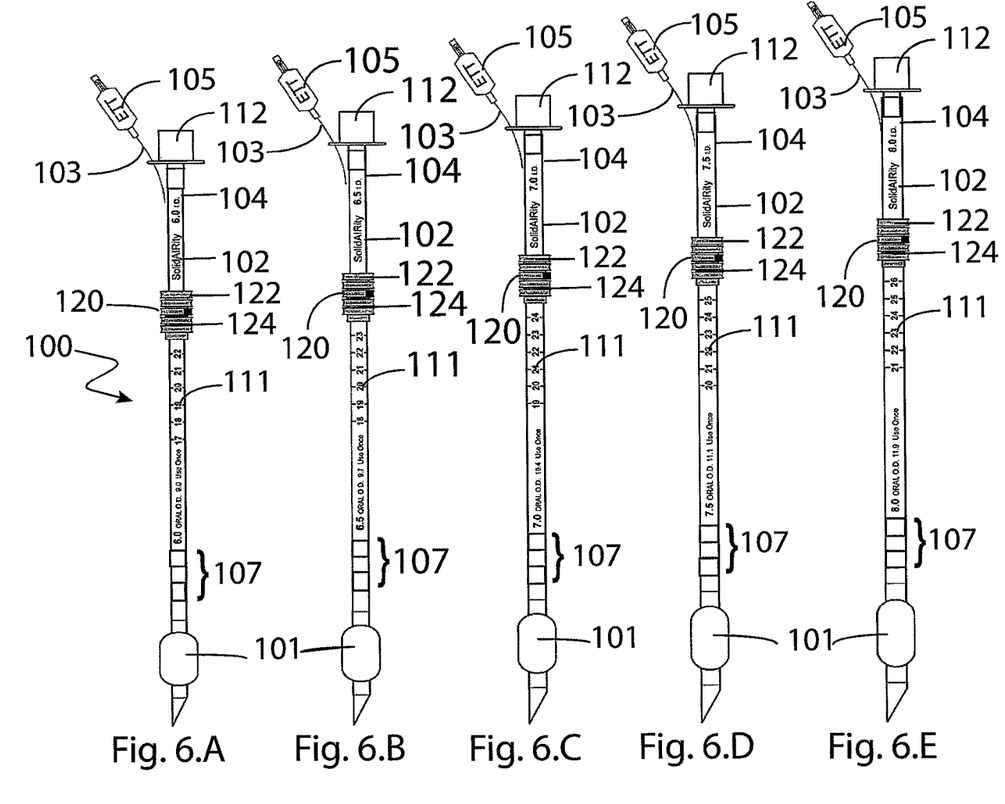

As shown in FIGS. 3, 4, and FIGS. 6.A.-6.E., 7.A.-7.D, 8.A. and 8.B., the KAD-collar has a plurality of ribs 122/122' formed thereon, each rib extending radially outwardly therefrom in the form of an annular flange. The KAD-collar may be formed integrally with the body or may be secured thereto by chemical bonding or other suitable means. The ribs 122/122' are positioned axially along the length of the KAD-collar 120/120', there being a uniform or substantially uniform distance between each of the ribs forming spaces or structural recesses 124/124' there between. At least one of the plurality of ribs 122/122', in an embodiment, preferably the middle rib 108 of the plurality of ribs, is marked to distinguish it from the other of the plurality of ribs formed thereon for position monitoring, as will be discussed later. The inwardly-extending annular flanges 72 and structural recesses 74 of the restraining tower 30 are structured and arranged to releaseably engage corresponding structural recesses 12/124' and outwardly-extending ribs 122/122' of the KAD-collar to interlock with one another when the c-shaped collars 32, 34 are locked together around the KAD-collar. In the locked position, multiple points of contact and interaction between the stabilizer's restraining tower and the KAD-collar are created by the interlocking ribs and recesses in the collar and the restraining tower, which prevent clinically significant movement of the airway device in response to substantial forces which may be applied thereto in any direction. The series of reference or depth markers or bands 111 extending circumferentially about the airway device facilitate initial placement of the device in a patient's airway with reference to a patient's upper incisors, as will be discussed in greater detail below.

Once the c-collars 32, 34 of the restraining device tower 30 are secured around the KAD-collar 120 as described above, it will be appreciated that the collar and restraining device interact to completely encapsulate the airway device to form a complete barrier to and thereby prevent any clinically significant movement of the airway device without applying any constricting, pinching or crushing forces to the airway device which would constrict the internal diameter thereof and, thus, reduce or restrict the supply of oxygen to a patient. Moreover, the restraining tower and the KAD-collar are situated outside of a patient's oral cavity, thereby minimizing risk of oral and/or dental injury to a patient.

Although it is important for the physician to determine the correct airway device or endotracheal tube size for every individual adult patient, most clinicians responsible for the intubation determine endotracheal tube size based upon an educated guess, rather than upon scientific formula, algorithm or accurate measurement of any kind. Some practitioners will choose to place a 7.5 mm endotracheal tube for all females and an 8.0 mm endotracheal tube for all males. Some will choose a 7.0 mm tube for small adults, a 7.5 mm tube for medium size adults and an 8.0 mm tube for large adults. Others may just get a so-called "feel" for the "appropriate" size tube they think a person may need based on their physical characteristics such as height, weight and general size appearance. No generally accepted and widely utilized method, formula, or system exists that maximizes the probability of choosing the optimally-sized endotracheal tube for adults. However, in practice, standard endotracheal tube sizes for adults, defined herein as "standard adult size airway devices" are generally considered to fall in a range of approximately 6.0 to 8.0 mm.

Figure 7:
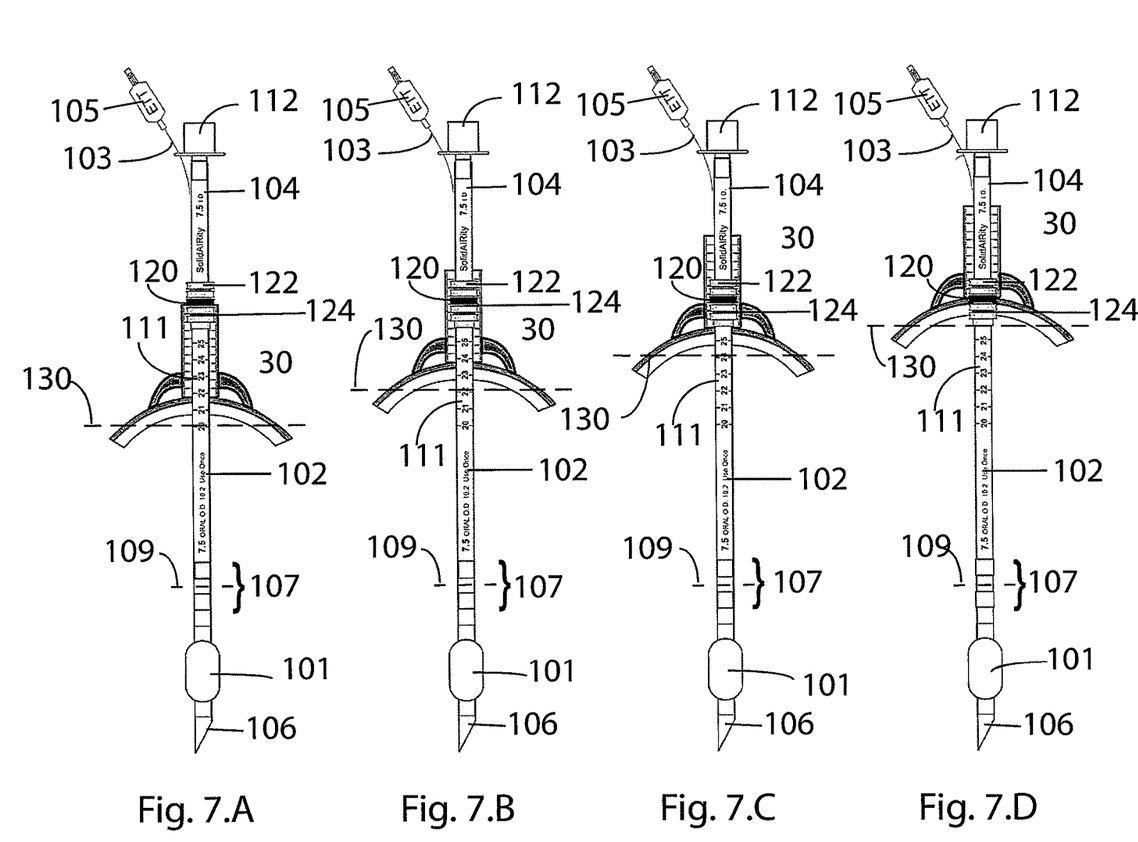
Figure 8:
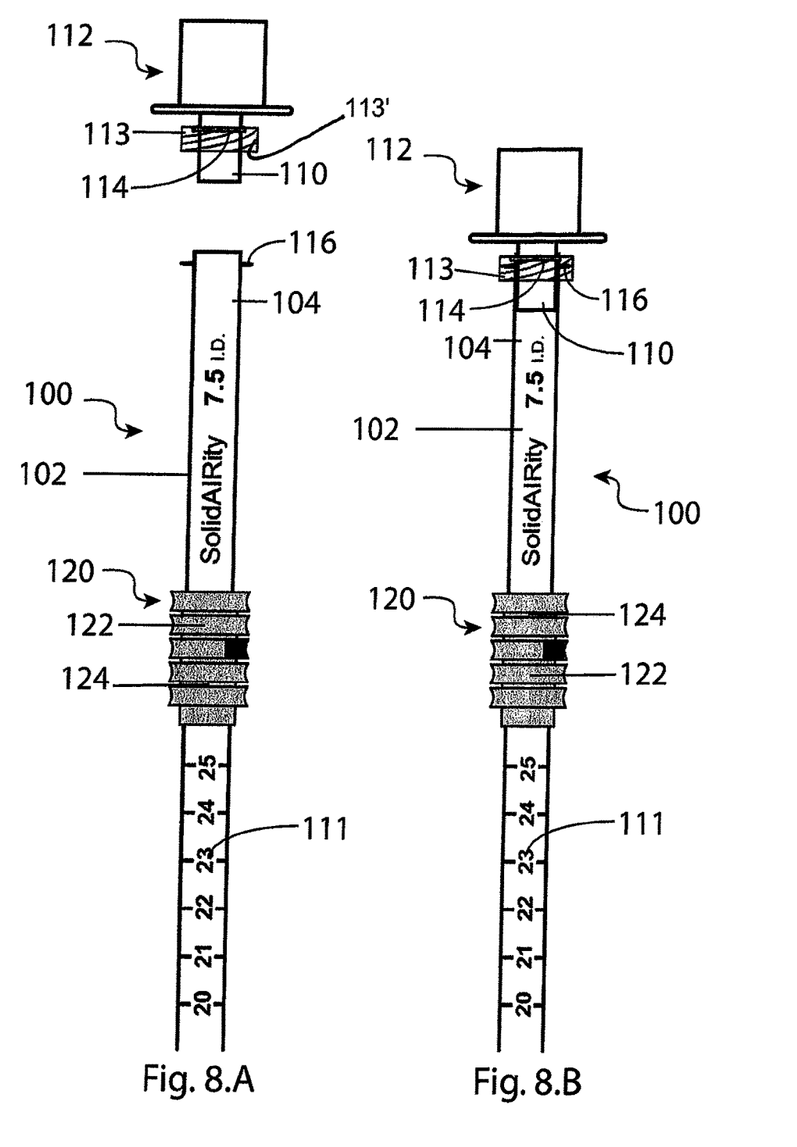

As shown in FIGS. 6.A.-6.E. and FIG. 7.A-7.D., the retention structure 120 is situated on each size endotracheal tube (6.0 mm, 6.5 mm, 7.0 mm, 7.5 mm and 8.0 mm) in a predetermined position on the tube to ensure that when a reasonably sized endotracheal tube is properly positioned in a patient's trachea, the retention collar ribs 122 will reside outside the patient's oral cavity and at least two ribs of the retention collar will interface with the recesses of the restraining tower 30. The airway stabilization system herein disclosed is designed to ensure that a maximum number of KAD-collar flanges or ribs 122 are enclosed within the stabilizer restraining tower 30 when the physician chooses a reasonably sized tube and properly positions the tube by placing the endotracheal tube with the depth positioning bands 107 at the level of the vocal cords. In addition, it is designed to ensure that even if a suboptimal size tube (too large or too small) is chosen and the tube is properly positioned by proper use of the depth positioning bands 107, that at least two ribs will be enclosed within the stabilizer restraining tower, to ensure that the tube remains in its intended position.

FIGS. 7.A.-D. illustrate the positioning of a standard 7.5 mm endotracheal tube with the depth positioning bands 107 affixed to a distal end portion thereof properly placed relative to the vocal cords, in a series of adults with differing length airways, as measured from the level of a patient's upper incisors 130 to the level 109 of a patient's carina (not shown). The different airway lengths result in the endotracheal tube position markers 111, at the level of the patient's incisors 130 varying from 20 cm FIG. 7A., to 22 cm FIG. 7B., to 24 cm FIG. 7C., to 26 cm FIG. 7D. Despite this significant variance in positioning of the endotracheal tube relative to the patient's upper incisors, due to the variations in length of different patient's tracheas and oral cavities, all positions allow for at least two ribs being enclosed in the restraining tower and thus adequate restraint of the endotracheal tube.

In practice, a clinician chooses the appropriate airway device tube size based on his or her clinical experience. The same variations in positioning, as shown in FIG. 7.A.-7.D. for a 7.5 mm endotracheal tube, may also be generated for all tube sizes. Importantly, a correctly sized airway device placed properly will typically have 3-4 ribs engaged, and the likelihood of one or fewer ribs being engaged even with an improperly sized tube is very small, much less than 1%.

Figure 9:
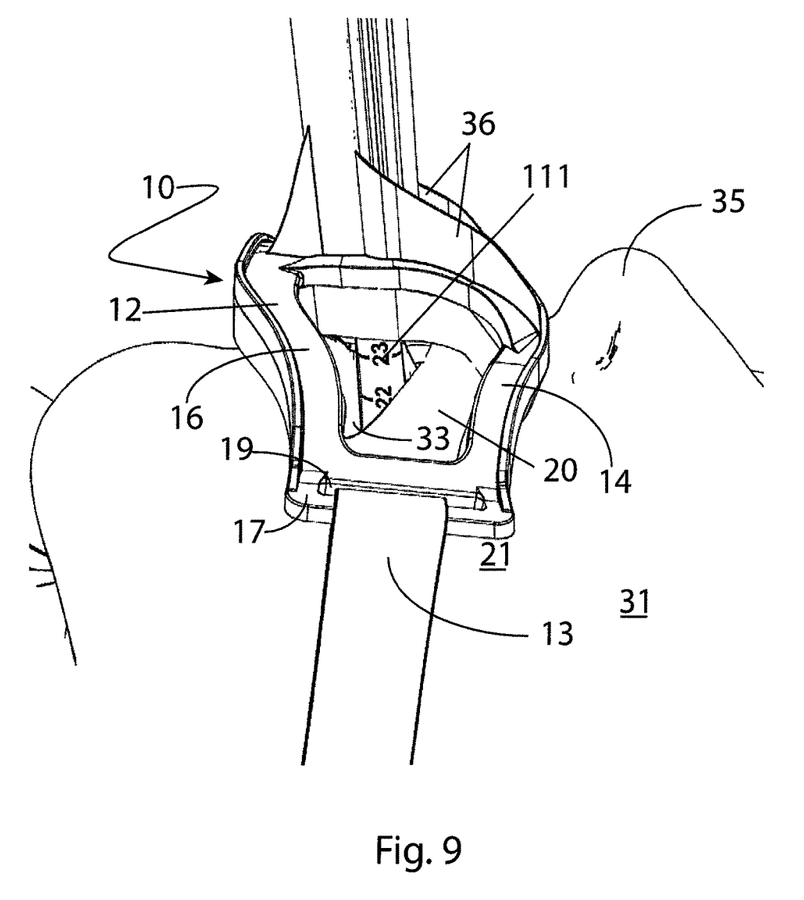
FIG. 9 is a side elevation view of an airway stabilization system of the present invention illustrating positioning confirmation with respect to a patient's upper incisors.
Figure 10:
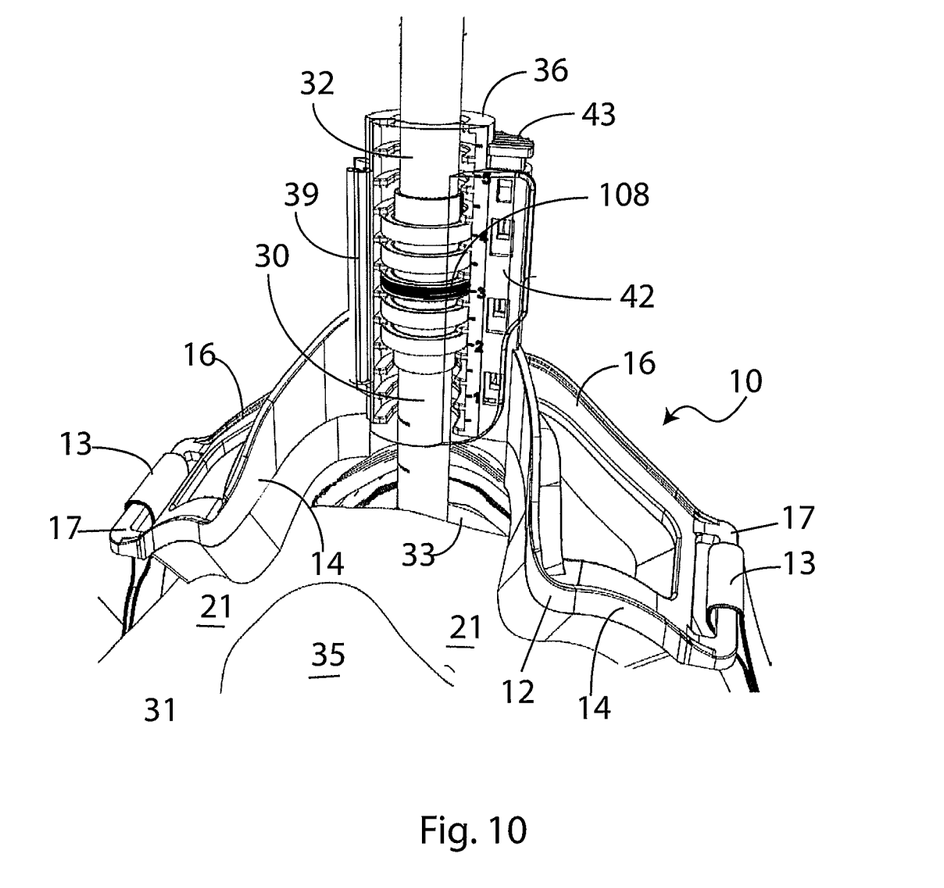
FIG. 10 is a perspective view an airway stabilization system of the present invention as seen from the top of a patient's head illustrating post-stabilization positioning confirmation via positioning of a depth indicator line on an airway device relative to reference markings on a stabilization device.

Referring to FIGS. 9 and 10, following positioning of an airway device 100 in a patient's trachea at a correct depth, a securing apparatus or stabilizer 10 as herein described may be releaseably attached to the airway device via releaseable engagement with a retention structure or KAD-collar 120 secured thereto. The relative position of the retention structure, and, accordingly, the airway device, in relation to the relative position of the stabilizer, may be monitored to ensure that the relative positions do not change by observing the position of the at least one marked middle rib 108 of the plurality of ribs 122 positioned axially along the length of the KAD-collar 120 with respect to the plurality of spaced apart reference markings or depth guides 50 are formed on c-collar 34. Should a change in these relative positions be observed, the practitioner may depress the quick-release actuator or button 43 to easily open the KAD-collar and adjust the relative positions of the stabilizer and the KAD-collar without interrupting ventilation of the patient.

GENERAL INTERPRETATION OF TERMS

In understanding the scope of the present invention, the term "configured" as used herein to describe a component, section or part of a device that is constructed to carry out the desired function. In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An airway stabilization system for maintaining an airway in a patient's trachea, the patient having a head, a face, cheeks, a mouth, an oral cavity, a chin, vocal cords, and a carina, the system comprising: an airway device adapted to be maintained in a preselected position in the patient's trachea and including a flexible body portion extending along an axis and having a preselected length and preselected internal and external diameters, a distal end portion adapted to be positioned a preselected distance from the patient's carina, and a proximal end portion adapted to be positioned outside of the patient's oral cavity; a retention structure secured to the proximal end portion of the airway device and adapted to be positioned outside of the patient's oral cavity, the retention structure having a preselected length; a securing apparatus adapted to be secured to the patient, the securing apparatus including a restraining device having a length and being adapted to releaseably engage the retention structure outside the patient's oral cavity whereby the risk of oral and dental injury to the patient is minimized, the securing apparatus and the retention structure cooperating with one another and being adapted to form a barrier to movement of the airway device in the patient's trachea in response to the application of multidirectional forces to the airway device; the retention structure and securing apparatus further cooperating to encapsulate a portion of the airway device circumferentially along the length of the restraining device whereby the encapsulated portion of the airway device is isolated from any constricting, pinching or crushing forces which would constrict the internal diameter of the airway device, wherein the retention structure includes a plurality of ribs formed thereon, each of the plurality of ribs extending radially outwardly therefrom in the form of an annular flange, the plurality of ribs being positioned axially along the length of the retention structure having a uniform or substantially uniform spacing distance therebetween, forming a plurality of spaces or structural recesses positioned axially along the length of the retention structure, wherein at least one of the plurality of ribs formed on the retention structure is marked to distinguish the at least one of the plurality of ribs from the other of the plurality of ribs formed thereon, wherein the securing apparatus includes a faceplate adapted to be secured to the patient and defining a plane, wherein the restraining device includes a pair of oppositely disposed, pivotally interconnected, c-shaped collars respectively extending generally symmetrically about and along an axis in a direction substantially perpendicular to the plane defined by the faceplate and adapted to be away from the patient's face, and wherein at least one of the pair of c-shaped collars includes a plurality of insertion depth guides affixed thereto.

2. The airway stabilization system of claim 1 wherein the faceplate includes an attachment apparatus adapted to extend around the patient's head adapted to attach the faceplate to the patient.

3. The airway stabilization system of claim 1 wherein each of the collars defines a semi-cylindrically shaped cavity about the axis of the collar, each cavity having first and second end portions, an outer surface, an inner surface, a pair of generally parallel extending edge surfaces, each of the collars including a plurality of spaced-apart annular flanges extending substantially radially inwardly from the inner surface thereof, each annular flange cooperating with an adjacent annular flange to define a structural recess therebetween.

4. The airway stabilization system of claim 3 wherein the inwardly extending annular flanges and structural recesses are structured and arranged to releaseably engage the plurality of structural recesses and outwardly extending annular flanges or ribs of the retention structure, whereby multiple points of contact and interaction between the securing apparatus and the retention structure are created which prevent clinically significant movement of the airway device in response to forces which may be applied thereto in any direction.

5. The airway stabilization system of claim 4 wherein the multiple points of contact and interaction between the securing apparatus and the retention structure are created by rotating at least one of the pivotally interconnected c-shaped collars about the axis of the collar into locking engagement with the other of the c-shaped collars from a side of the airway device, whereby the airway device remains connected to a ventilation source and ventilation of the patient is uninterrupted.

6. The airway stabilization system of claim 4 further including a locking mechanism far-adapted to releaseably clamp the pivotally interconnected c-shaped collars together circumferentially around the retention structure secured to the airway device in stabilizing and supporting engagement therewith.

7. The airway stabilization system of claim 1 wherein at least one of the pivotally interconnected c-shaped collars includes a plurality of spaced apart depth indicator markings formed thereon, the markings being structured and arranged to cooperate with at least one marked rib formed on the retention structure to indicate a relative position of the retention structure with respect to a position of the restraining device, whereby the relative positions of the retention structure and the restraining device are monitored to ensure that the relative positions do not change.

8. The airway stabilization system of claim 7 further including, a plurality insertion depth mark indicators affixed to a distal end portion of the airway device.

9. The airway stabilization system of claim 8 wherein each of the series of insertion depth mark bands is luminescent in color, whereby visualization of the depth mark bands during positioning of the airway device is enhanced.

10. The airway stabilization system of claim 6 further including a vertical bar formed in at least one of the plurality of c-shaped collars and adapted to prevent the rotation of the retention collar within the restraining device whereby the internal diameter of the airway device remains unobstructed.

11. The airway stabilization system of claim 1 wherein the securing apparatus includes a faceplate adapted to be secured to a patient's face, the faceplate including at least one aperture formed therein and adapted to permit access to a patient's oral cavity.

12. The airway stabilization system of claim 1 wherein the airway device is an endotracheal tube.

13. The airway stabilization system of claim 1 wherein the airway device is a supraglottic airway device.

14. The airway stabilization system of claim 6 wherein the locking mechanism includes a quick release actuator structured and arranged to release the pivotally interconnected c-shaped collars after they have been clamped together.

15. The airway stabilization system of claim 1 further including a vertically extending channel formed in at least one of the plurality of c-shaped collars and being adapted to prevent the rotation of the retention collar within the restraining device whereby the internal diameter of the airway device remains unobstructed.

* * * * *